United States Patent [19]

McDonald

[11] 4,063,310
[45] Dec. 13, 1977

[54] SAMPLER CONTROL SYSTEM FOR CHROMATOGRAPH ANALYTICAL APPARATUS

[75] Inventor: John Marshall McDonald, Cambridge, England

[73] Assignee: Pye Limited, England

[21] Appl. No.: 699,073

[22] Filed: June 23, 1976

Related U.S. Application Data

[63] Continuation-in-part of Ser. No. 489,832, July 18, 1974, abandoned.

[30] Foreign Application Priority Data

July 25, 1973 United Kingdom ............... 35368/73

[51] Int. Cl.$^2$ ...................... G06F 7/28; G06F 15/06; G06F 15/46
[52] U.S. Cl. .................................... 364/900; 73/23.1; 73/61.1 C
[58] Field of Search .......... 340/172.5, 173 SP, 173 R; 445/1; 73/61.1 C, 61.1 R, 423 A, 23.1; 235/151.3, 92 K, 92 EA, 92 DP

[56] References Cited

U.S. PATENT DOCUMENTS

| | | |
|---|---|---|
| 3,508,442 | 4/1970 | Lightner et al. ................... 73/423 A |
| 3,753,243 | 8/1973 | Ricketts, Jr. et al. ............ 340/172.5 |
| 3,772,659 | 11/1973 | DeVries ............................. 340/172.5 |
| 3,794,970 | 2/1974 | Pearson et al. .................... 340/172.5 |
| 3,798,612 | 3/1974 | Struger et al. ..................... 340/172.5 |
| 3,810,118 | 5/1974 | Kiffmeyer .......................... 340/172.5 |
| 3,827,030 | 7/1974 | Seipp .................................. 340/172.5 |
| 3,875,564 | 4/1975 | Thuruoka et al. ................ 340/172.5 |

Primary Examiner—Melvin B. Chapnick
Attorney, Agent, or Firm—Frank R. Trifari; Steven R. Biren

[57] ABSTRACT

An automatic liquid sampler for a gas chromatograph includes a sampling mechanism and a control system which controls both the sampling mechanism and other functions of the chromatograph. Four sub-programs are stored in an integrated circuit read-only memory. A complete program for analyzing a series of samples consists of a sequence of the sub-programs read out by a counter under the control of a logic switch unit connected between the final stages of the counter and the most significant address inputs of the memory. The logic switch unit includes a rotary wafer switch which can be manually set to one of twelve positions each corresponding to a unique complete program made up from the sub-programs according to the wiring of the switch.

4 Claims, 3 Drawing Figures

SAMPLER CONTROL SYSTEM FOR CHROMATOGRAPH ANALYTICAL APPARATUS

This is a continuation-in-part of application Ser. No. 489,832, filed July 18, 1974, now abandoned.

BACKGROUND OF THE INVENTION

This invention relates to control systems for analytical apparatus. It also relates to automatic liquid samplers, for chromatographic apparatus, of the type including a sampling mechanism and a control system which controls both the sampling mechanism and other functions of the apparatus.

In a known automatic liquid sampler for the routine analysis of similar samples by gas chromatography, the samples are contained in vials carried on a turntable which may be indexed to bring each vial in turn to a sampling position. An injection syringe is lowered until its needle enters the vial at the sampling position and the plunger is then operated to fill the syringe. To ensure complete filling and the absence of air bubbles, the plunger is moved up and down several times. The syringe is then raised to clear the vial, traversed laterally to a position above the chromatograph column, and lowered until the needle penetrates the septum of the column. The plunger is operated to inject the sample into the column and the analysis commences. When the analysis of a given sample is completed, the turntable is indexed to bring a fresh sample to the sampling position and the sequence is repeated.

The various movements of the turntable, syringe body and plunger are produced by solenoid actuators which are energized as required by logic circuits controlled by a program unit including a punched tape reader. The program unit also controls the operation of ancillary apparatus such as chart recorders, integrators etc. responsive to the output of the chromatograph detectors. A plurality of tapes are provided, each punched with a program for the analysis of samples of a given type, and for repetitive analyses a tape may be formed into a closed loop.

SUMMARY OF THE INVENTION

An object of this invention is to provide a control system for analytical apparatus, for furthermore an automatic liquid sampler for chromatographic apparatus, in which the information necessary for carrying out a plurality of selected programs is stored in a read-only memory, preferably an integrated circuit read only memory instead of a plurality of punched tapes.

According to the invention there is provided a control system for an analytical apparatus, including an integrated circuit read-only memory containing a plurality of sets of words arranged so that the address for each word is derived from a first group of memory inputs which determines the set and a second group of memory inputs which determines the word within the set, a counter arranged with stages thereof connected to the second group of memory inputs so that a cycle of the counter through said stages will read out a set of words from the memory in sequence corresponding to a sub-program of operations of the apparatus, and program selection means arranged with outputs thereof connected to the first group of memory inputs so that a selected sequence of conditions on said outputs, one condition for each said cycle of the counter, corresponds to a complete program of operations of the apparatus.

Preferably in such a control system, the program selection means includes a logic switch unit settable to a plurality of positions, each position corresponding to a complete program, said stages of the counter connected to the second group of memory inputs from an initial set of stages of the counter, and the program selection means also includes the remaining, final, stages of the counter connected to inputs of the logic switch unit, the arrangement being such that the particular sub-program of operations produced by a cycle of the counter through the initial stages is determined by the setting of the logic switch unit and the condition of the final stages of the counter, and such that a complete program consists of a repeated series of sub-programs.

At the end of each sub-program there can be included a "hold" command which is operative or not according to the setting of the logic switch unit and the condition of the final stages of the counter, the arrangement being such that an operative "hold" command delays the start of the next sub-program until it is cancelled by a signal from a timer.

A control system with each sub-program including a hold command as described in the previous paragraph is particularly suitable for incorporation with a sampling mechanism in an automatic liquid sampler for chromatographic apparatus. In such a sampler, according to the invention, each sub-program includes a unique manner of operation of the sampling mechanism, and in which one of more sub-programs also provide for operation of other functions of the apparatus, whereby a particular position to which the logic switch unit is set will determine a respective complete program of operations effecting the automatic analysis by the apparatus of a series of samples.

BRIEF DESCRIPTION OF THE DRAWING

The invention will now be described in more detail with reference to the accompanying drawing; in which.

DETAILED DESCRIPTION

Figure 1:
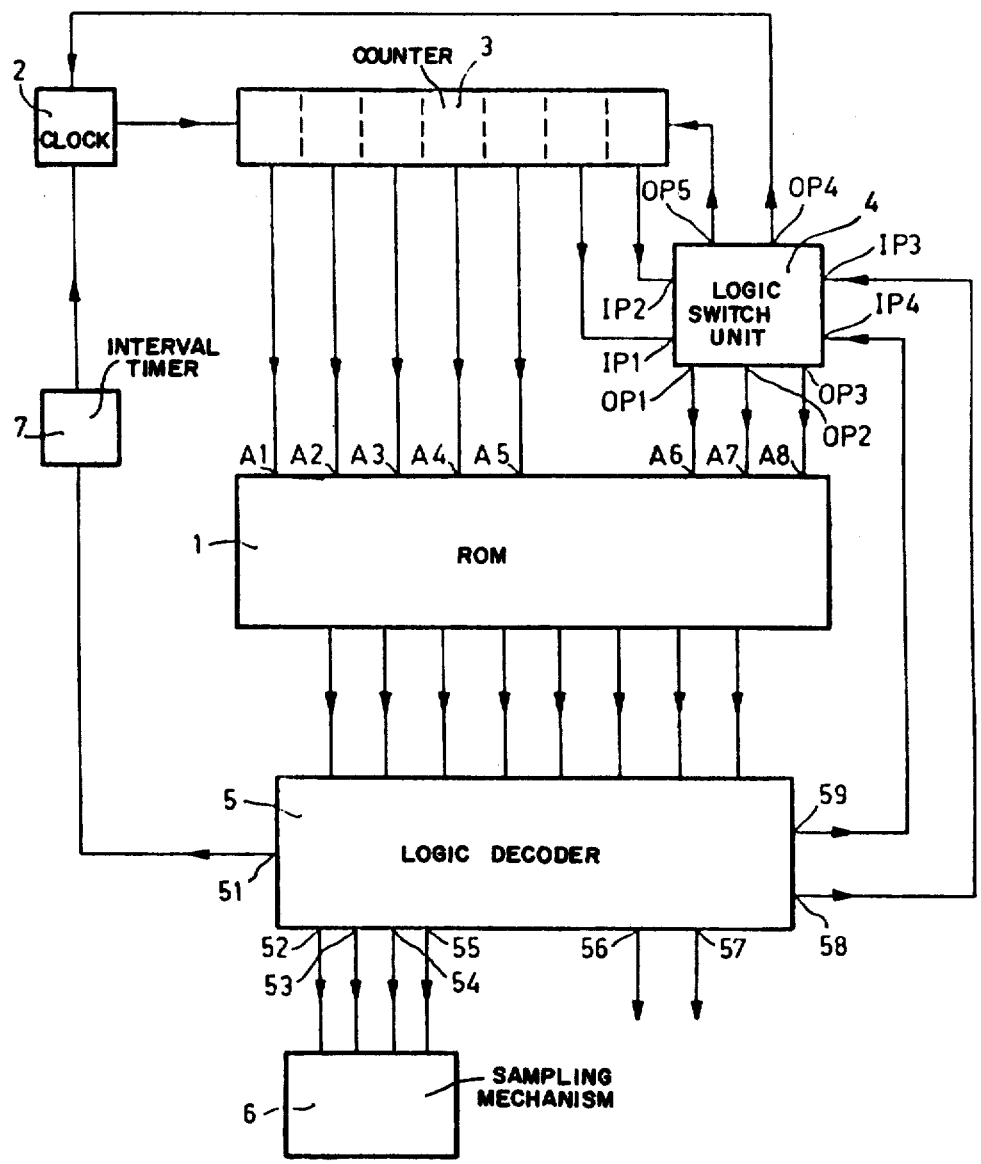
FIG. 1 shows a schematic diagram of a control system according to the invention and a sampling mechanism which together constitute an automatic liquid sampler for chromatographic apparatus according to the invention.

Referring now to FIG. 1, a read-only memory 1 is a commercially available integrated circuit memory having a capacity of 256 words of 8 bits each. For reasons which will be explained later, only half the capacity is used, and the memory is arranged to store 4 sets of words having 32 words in each set with the address for each word being derived from the three memory inputs A6, A7, A8 which determine the set and from the five memory inputs A1, A2, A3, A4, A5 which determine the word within the set. A 2-second clock 2 feeds a seven-stage counter 3 of which the initial five stages (i.e. divide by 32) are connected to the memory inputs A1 to A5 respectively, and the final two stages (i.e. divide by 4) are connected, via a logic switch unit 4, to the memory inputs A6 to A8. The logic switch unit 4 is settable to a plurality of positions, as will be explained later in more detail with references to FIG. 2. A cycle of the counter 3 through the initial five stages will read out a set of 32 words from the memory in sequence into a logic decoder 5 which will produce control signals on its outputs 51 to 59 to effect a sub-program of operations. Decoder 5 is typically an SN 7442 type TTL BCD-to-decimal decoder integrated circuit. As shown in FIG. 1, control signals on outputs 52, 53, 54, and 55 operate a sampling mechanism 6 of a gas chromatograph, control signals on outputs 56 and 57 effect the operation of other functions of the chromatograph, e.g. a chart recorder (not shown), the control signal on output 51 operates an interval timer 7 which is connected to the clock 2, and control signals on outputs 58 and 59 are fed back to the logic switch unit 4. the interval timer is known in the art, and may be constructed from a chain of SN 7490 decade counters.

Figure 3:
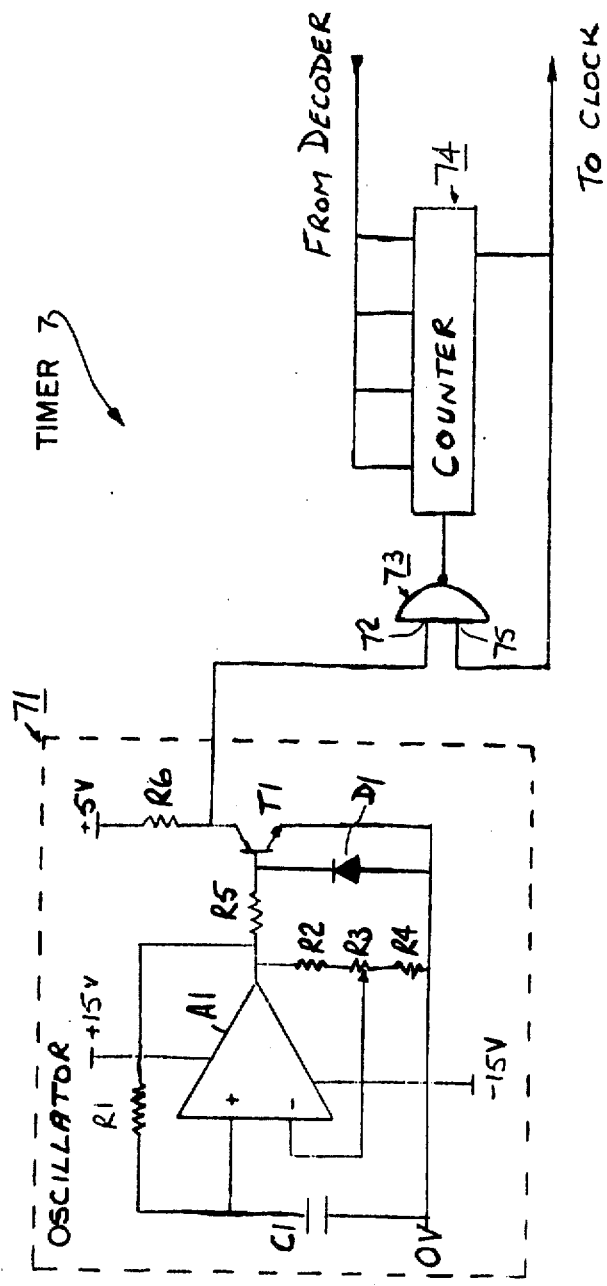
FIG. 3 shows the timer shown in FIG. 1 in greater detail.

As shown in FIG. 3 the interval timer 7 comprises an oscillator 71 whose output is connected to a first input 72 of a NAND gate 73 which may conveniently be part of an SN 7400 TTL quad 2-input NAND gate integrated circuit. The output of the NAND gate 73 is connected to the clock input of a counter 74. The counter 74 may be constructed, for example as four series connected type SN 7490 TTL decade counter integrated circuits. The control signal from output 51 of the decoder 5 is connected to the reset input of each of the counter stages. The output of the last stage of the counter chain is connected to a second input 75 of the NAND gate 73.

The oscillator 71 comprises an operational amplifier A1 which may be one half of a type 747 dual operational amplifier integrated circuit which has a non-inverting input (+) and inverting input (−). The non-inverting input of the amplifier A1 is connected to the junction of a capacitor C1 and resistor R1. The other end of the capacitor R1 is connected to OV while the other end of resistor R1 is connected to the output of amplifier A1. The series arrangement of a resistor R2, a potentiometer R3, and a resistor R4 is connected between the output of amplifier A1 and OV, the slider of the potentiometer R3 being connected to the inverting input of the amplifier A1. The output of amplifier A1 is further connected via a resistor R5 to the base of an npn transistor T1, the junction of the base of transistor T1 and resistor R5 being connected to OV via a diode D1. The emitter of transistor T1 is connected to OV while the collector is connected to ±5V via a resistor R6.

The operation of the oscillator 71 is as follows. Since the amplifier A1 has a very high gain any imbalance between the voltages at its inputs will cause the output to go to ±15V depending on the direction of imbalance. This will cause capacitor C1 to be charged towards ±15V via resistor R1. When the voltage across the capacitor C1 exceeds that at the inverting input of the amplifier A1 the output of the amplifier A1 will switch from the one extreme voltage to the other thus causing capacitor C1 to begin charging to the opposite polarity and the whole process is repeated. The value of capacitor C1 and resistor R1 determine the frequency of oscillation with a fine frequency control being provided by potentiometer R3. It will be noted that the total voltage swing at the output of amplifier A1 is from −15V to +15V. These voltage levels would damage the TTL integrated circuits forming the NAND gate 73 and counter 74. To bring this voltage swing to a suitable level to drive the NAND gate 73 and counter 74 a buffer circuit which comprises resistor R5, diode D1, transistor T1, and resistor R6 is connected to the output of amplifier A1. The diode D1 is provided to protect the transistor from the effects fo the negative voltage peaks produced at the output of amplifier A1.

The operation of the timer is as follows. In order to start the timer the signal from the decoder 5 resets the counter which causes an inhibit signal to be applied to the clock 2 from the output of the counter. The reset signal then disappears and the counter 74 is driven by the oscillator 71 until the output of the last stage changes state. The change of state of the last stage of the counter causes a signal to appear at its output which releases the inhibit on the clock 2 and inhibits the NAND gate 73 thus preventing the counter from cycling further.

It would be possible to use other oscillator circuits to drive the counter 74, for example a multivibrator and to use other types of timers in place of the timer disclosed. For example an RC network or a cam timer driven by a synchronous motor could be used.

The particular sub-program of operations produced by a cycle of the counter 3 through the initial five stages depends on the condition on the memory inputs A6 to A8 during that cycle, which is determined by the condition of the final two stages of the counter 3 and the setting of the logic switch unit 4. Normally, the clock pulse following the completion of a cycle through the initial five stages of the counter sets the final two stages to a new condition and hence starts the next sub-program of operations according to the setting of the logic switch unit 4. Thus a complete program normally consists of a series of four sub-programs which is repeated for each complete cycle of the seven-stage counter 3.

Two refinements of the process described in the previous paragraph will now be briefly mentioned, and their significance will be explained in more detail later. First, there is included at the end of each sub-program a "hold" command which produces a control signal on the output 58 of the decoder 5. This control signal will, or will not, produce a signal on the output OP 4 of the logic switch unit 4 depending on the setting of the unit 4 and the condition of the final two stages of the counter 3. If there is a resulting signal on the output OP 4, i.e. if the "hold" command is operative, then this signal, which is fed to the clock 2, will delay the start of the next sub-program until it is cancelled by a signal from the interval timer 7. Second, there is also included at the end of each sub-program a "reset counter" command which produces a control signal on the output 59 of the decoder 5. This control signal will, or will not, produce a signal on the output OP 5 of the logic switch unit 5 depending on the setting of the unit 4 and the condition of the final two stages of the counter 3. If there is a resulting signal on the output OP 5, i.e. if the "reset counter" command is operative, then this signal will reset the counter, and so the series of sub-programs which is repeated to form the complete program corresponds to less than a complete cycle of the seven-stage counter 3.

The sampling mechanism 6 includes a sample holder, e.g. a turntable, for holding a plurality of sample containers and indexing them to a sampling position, and a syringe mechanism for extracting samples from said containers and injecting them into the chromatograph column.

The four sub-programs stored in the memory 1 each include a unique manner of operation of the sampling mechanism as outlined below.

Sub-program A — turntable advance, flush syringe with sample, inject sample.

Sub-program B — flush syringe with sample, inject sample.
Sub-program C — turntable advance, flush syringe with wash liquid leaving empty and raised.
Sub-program D — turntable advance, flush syringe with wash liquid leaving full and lowered.

Sub-programs A and B will flush the syringe 6 times prior to filling for injection and sub-programs C and D will flush the syringe 8 times with the wash liquid.

Sub-programs A and B also provide for operation of functions of the chromatograph other than the sampling mechanism.

The details of sub-programs A and C are given by way of example in the tables below.

| | T sec. | SUB-PROGRAM A Syringe Movements | Other Functions |
|---|---|---|---|
| 0 | 0 | — | — |
| 1 | 4 | — | Stop integrator |
| 2 | 8 | — | Sample Advance |
| 3 | 12 | Syringe ↓ | Mark 10's |
| 4 | 16 | Plunger ↑ | " |
| 5 | 20 | — | " |
| 6 | 24 | Plunger ↓ | " |
| 7 | 28 | Plunger ↑ | — |
| 8 | 32 | — | Mark 1's |
| 9 | 36 | Plunger ↓ | " |
| 10 | 40 | Plunger ↑ | " |
| 11 | 44 | — | " |
| 12 | 48 | Plunger ↓ | — |
| 13 | 52 | Plunger ↑ | — |
| 14 | 56 | — | — |
| 15 | 60 | Plunger ↓ | — |
| 16 | 64 | Plunger ↑ | — |
| 17 | 68 | — | — |
| 18 | 72 | Plunger ↓ | — |
| 19 | 76 | Plunger ↑ | — |
| 20 | 80 | — | — |
| 21 | 84 | Plunger ↓ | — |
| 22 | 88 | Plunger ↑ | — |
| 23 | 92 | — | — |
| 24 | 96 | — | Auto Zero |
| 25 | 100 | Syringe ↑ | Clock Fast |
| 26 | 102 | Syringe → | — |
| 27 | 104 | Syringe ↓ | — |
| 28 | 106 | Plunger ↓ | Inject, Start Integrator Start Timer |
| 29 | 208 | Syringe ↑ | — |
| 30 | 110 | Syringe ← | Hold Clock, Slow Clock |
| 31 | 112 | — | Reset Counter |

| | T sec. | SUB-PROGRAM C Syringe Movements | Auxiliary Functions |
|---|---|---|---|
| 0 | 0 | — | — |
| 1 | 4 | — | — |
| 2 | 8 | — | Sample advance |
| 3 | 12 | Syringe ↓ | — |
| 4 | 16 | Plunger ↑ | — |
| 5 | 20 | — | — |
| 6 | 24 | Plunger ↓ | — |
| 7 | 28 | Plunger ↑ | — |
| 8 | 32 | — | — |
| 9 | 36 | Plunger ↓ | — |
| 10 | 40 | Plunger ↑ | — |
| 11 | 44 | — | — |
| 12 | 48 | Plunger ↓ | — |
| 13 | 52 | Plunger ↑ | — |
| 14 | 56 | — | — |
| 15 | 60 | Plunger ↓ | — |
| 16 | 64 | Plunger ↑ | — |
| 17 | 68 | — | — |
| 18 | 72 | Plunger ↓ | — |
| 19 | 74 | Plunger ↑ | — |
| 20 | 80 | — | — |
| 21 | 84 | Plunger ↓ | — |
| 22 | 88 | Plunger ↑ | — |
| 23 | 92 | — | — |
| 24 | 96 | Plunger ↓ | — |
| 25 | 100 | Plunger ↑ | — |
| 26 | 104 | — | — |
| 27 | 108 | Plunger ↓ | — |
| 28 | 112 | Syringe ↑ | — |
| 29 | 116 | — | — |
| 30 | 120 | — | Hold Clock |
| 31 | 124 | — | Reset Counter |

The 256-word, 8 bits per word, memory 1 has been chosen for convenience from the commercially available integrated circuit read-only memories and could thus store eight sub-programs of 32 words each. The Intel 1702 is an example of such a ROM. However, the four sub-programs A, B, C and D, although occupying only half the memory 1, can be combined in selected sequences to provide a large number of different complete programs of operations effecting the automatic analysis by the chromatographic apparatus of a series of samples.

Twelve such complete programs are shown below:

```
Program  1  A, A, A, A, A, A, A, A,—
         2  A, B, A, B, A, B, A, B,—
         3  AC, AC, AC, AC,—
         4  AD, AD, AD, AD,—
         5  A, BC, A, BC,—
         6  A, BD, A, BD,—
         7  ACC, ACC,—
         8  A, BCC, A, BCC,—
         9  ACCC, ACCC,—
        10  CAC, CAC—
        11  CA, BC, CA, BC,—
        12  CACC, CACC,—
```

In the above sequences a comma (,) indicates that an operative "hold" command delays the next sub-program while the analysis takes place of a sample injected by a sub-program A or B. Thus, for example, program 1 provides for a single analysis from each sample on the turntable; program 2 provides for two analyses from each sample on the turntable; program 5 provides for two analyses followed by a wash according to sub-program C from each sample on the turntable, and program 8 provides for two analyses followed by two washes according to sub-program C from each sample on the turntable.

It will be seen that programs 1, 2, 3, 4, 8, 9, 11 and 12 are each effectively a repeated series of four sub-programs, i.e. each series is performed by a complete cycle of the seven-stage counter 3 of FIG. 1 and no operative "reset counter" commands are required. However, programs 5, 6, 7 and 10 are each effectively a repeated series of three sub-programs and so an operative "reset counter" command is required after every third sub-program.

In order to explain how the desired sequence of sub-programs is achieved consequent upon the selection of a particular complete program, the logic switch unit 4 will now be described in more detail.

Figure 2:
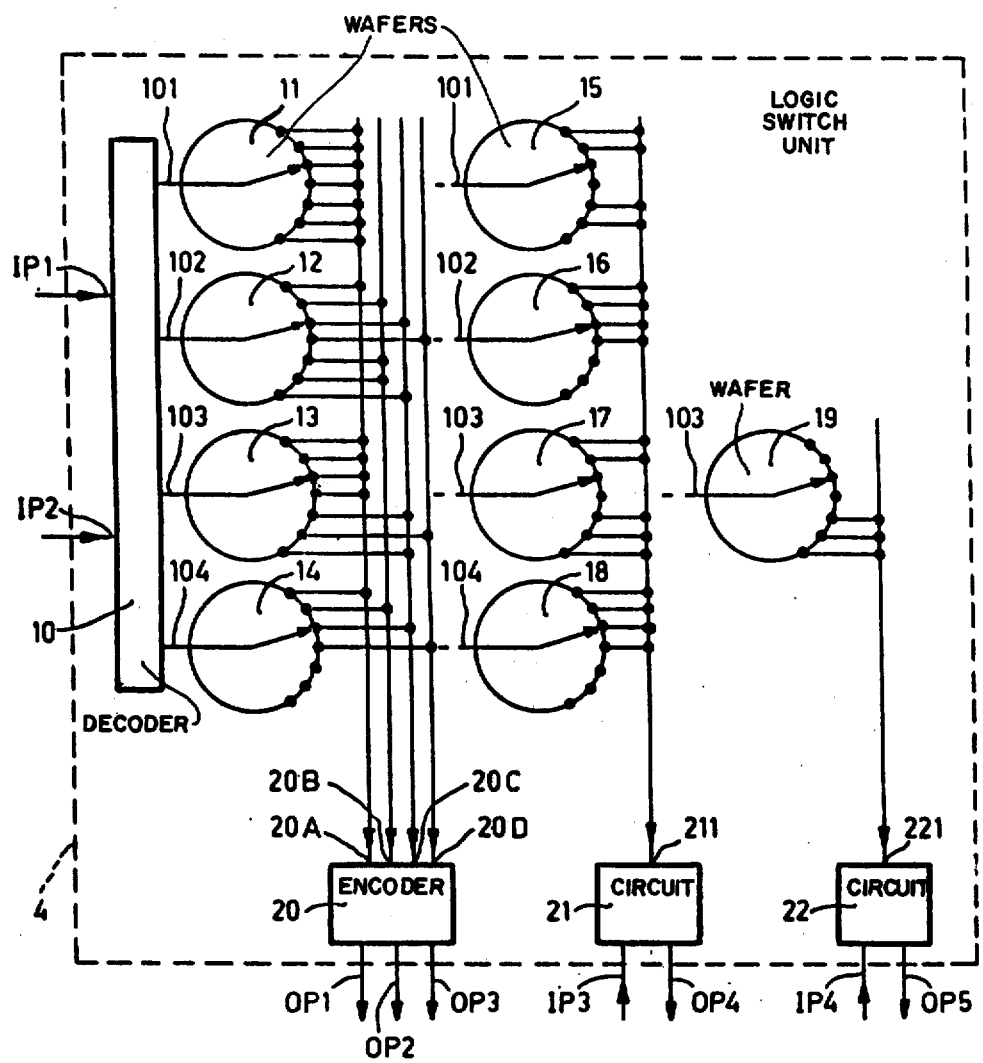
FIG. 2 shows a schematic diagram of the logic switch unit of FIG. 1, in greater detail.

Referring now to FIG. 2, the logic switch unit 4 includes a rotary wafer switch having nine wafers 11 to 19 and is manually settable to twelve different positions, each position corresponding to one of the twelve complete programs described above. For the sake of simplicity only positions 1 to 7 are shown in FIG. 2. A two-line to four-line decoder 10 is connected between the wafers 11 to 19 and the final two stages of the counter 3 via the inputs IP 1 and IP 2 of the unit 4, so that for each combination of conditions on the inputs IP 1 and IP 2 a signal is fed from the decoder 19 to a predetermined one or more wafers. More particularly, a complete cycle of the seven-stage counter 3 will produce an output on the line 101 connected to the wafers 11 and 15, followed by an output on the line 102 connected to the wafers 12 and 16, followed by an output on the line 103 connected to the wafers 13, 17 and 19, followed by an output on the line 104 connected to the wafers 14 and 18. The wafers 11 to 14 are wired to the inputs 20A, 20B, 20C and 20D of a four-line to three-line encoder 20 whose outputs are the outputs OP 1, OP 2 and OP 3 of the unit 4 (see FIG. 1). The standard component SN, an 8-line to 3-line priority encoder, may be used for this encoder. The wafers 15 to 18 are wired to the control input 211 of a circuit 21 to which the input IP 3 and the output OP 4 (see FIG. 1) of the unit 4 are connected. The wafer 19 is wired to the control input 221 of a circuit 22 to which the input IP 4 and the output OP 5 (see FIG. 1) of the unit 4 are connected. Circuits 21 and 22 may be the standard SN quad 2-input NAND gate component known in the art.

FIG. 2 shows, by way of example, the wafer switch set to position 3 corresponding to complete program 3. The operation of the unit 4 will now be described for this program. The first condition of the final two stages of the counter gives input conditions on IP 1 and IP 2 which produce an output on the line 101. The wafer 11 connects the line 101, in position 3, to the input 20A of the encoder 20 which produces conditions on the outputs OP 1, OP 2 and OP 3 which select sub-program A in the read-only memory 1. At the end of sub-program A a "hold" command signal is applied to the input IP 3 of the circuit 21; however, in position 3 of the wafer switch, the output on line 101 is not connected by wafer 15 to the control input 211 of circuit 21 and so there is no signal on output OP 4 and the "hold" command is not operative. The clock 2 (see FIG. 1) thus sets the final two stages of the counter 3 to its next condition without delay. In this next condition the output on line 102 is connected by wafer 12 to input 20C of the encoder 20 giving outputs on OP 1, OP 2 and OP 3 which select sub-program C. At the end of sub-program C, the "hold" command is operative because the output on line 102 is connected by wafer 16 to the control input 211 of circuit 21. The next two conditions of the final two stages of the counter give program A again via line 103 and wafer 13 at the end of which the "hold" command is not operative via line 103 and wafer 17, followed by program C again via line 104 and wafer 14 at the end of which the "hold" command is operative via line 104 and wafer 18. This completes the series of sub-programs, A, C, A and C, which is then repeated by the next complete cycle of the counter 3.

As has been previously mentioned in the description of the complete programs 1 to 12, an operative "reset counter" command is required after every third sub-program for programs 5, 6, 7 and 10. In FIG. 2 it can be seen that for positions 5, 6, 7 (and 10 not shown) the line 103 is connected to control input 221 of circuit 22. Thus although a "reset counter" command is included at the end of every sub-program and produces a signal on input IP 4 of circuit 22, the logic unit 4 is wired so that it is only operative in those sub-programs selected by an output on line 104 in programs 5, 6 and 7.

Twelve-position rotary wafer switches are commercially available and are convenient to use in the above-described arrangement since twelve programs should be enough to cover most uses of a gas chromatograph apparatus. However, it will be appreciated that more combinations of the four sub-programs in the read-only memory are possible and could be provided with a logic unit including a switch settable to more than twelve positions. Furthermore for a given set of sub-programs stored in the read-only memory and a given number of positions on the switch, say twelve, the nature of the twelve programs can be varied simply by varying the wiring within the switch.

A further possible variation within the scope of the invention is to have a program selection means which consists of the logic switch unit 4 driven by a computer instead of by the final two stages of the counter 3. This could provide for greater flexibility in the operation of the chromatograph, for example the computer could decide whether a particular analysis was a good one, and if not send the next signal to the unit 4 so as to repeat it.

What is claimed is:

1. A control system for analytical apparatus comprising:
   a read-only memory containing a plurality of sets of words, each set of words defining a sequence of operations of said apparatus;
   first and second groups of read only memory inputs;
   means for selecting a plurality of said sets of words one at a time in a selectable order to produce a composite sequence of operations of said apparatus comprising program selection means having a plurality of outputs connected to said first group of memory inputs; the program selection means comprising a logic switch unit settable to a plurality of states to produce a selected sequence of condition signals on said outputs of said program selection means;
   means for selecting one of said words within a selected one of said sets comprising a counter having a plurality of outputs connected to said second group of memory inputs; and
   means for cycling said counter, the consequent variation in the states of the counter outputs being effective to read out sequentially the words in the selected one of said sets of words during one cycle of said counter, said condition signals at each step of said sequence being present for one cycle of said counter.

2. A system as defined in claim 1, further comprising an automatic liquid sampler for a chromatographic apparatus having a chromatograph column, said sampler including a sampling mechanism, wherein each of said sequence of operations of said apparatus is operatively associated with the operation of said sampling mechanism, wherein at least one sequence of operations provides for operation of predetermined chromatographic functions and wherein a particular position to which said logic switch is set determines a respective program of operations of said apparatus of a series of supplied samples.

3. A control system for analytical apparatus comprising:
   a read-only memory containing a plurality of sets of words, each set of words defining a sequence of operations of said apparatus;
   first and second groups of read-only memory inputs;
   a counter having first and second groups of stages connected in cascade;
   means for selecting a plurality of said sets of words one at a time in a selectable order to produce a composite sequence of operations of said apparatus, comprising program selection means having a plurality of outputs connected to said first group of memory inputs, said program selection means comprising a logic switch unit settable to a plurality of states, each state corresponding to an operation program, the outputs of said second group of stages of said counter being connected to the inputs of said logic switch unit;

means for selecting one of said words within a selected one of said sets comprising the first group of stages of said counter having a plurality of outputs connected to said second group of memory inputs; and means for cycling said counter, the consequent variation in the states of said outputs of said first group of stages being effective to read out sequentially the words in a selected set during one cycle of said first group of stages of said counter, the particular set of words read out during one cycle of said first group of stages of said counter being determined by the setting of said logic switch unit and the condition of the second group of stages of said counter.

4. A control system for analytical apparatus as in claim 3, wherein said logic switch unit comprises decoder means for receiving the outputs of said second group of stages of said counter and for generating a plurality of decoder outputs representative thereof, switching means having a plurality of switching stages for receiving said decoder outputs and for providing a plurality of switched outputs which comprise the decoder outputs arranged in a selectable order, said switching means having a number of stages at least equal to the number of outputs of said decoder means, and encoder means for receiving said switched outputs and for generating therefrom said plurality of outputs connected to said first group of memory inputs.

* * * * *

UNITED STATES PATENT AND TRADEMARK OFFICE
CERTIFICATE OF CORRECTION

PATENT NO. : 4063310
DATED : December 13, 1977
INVENTOR(S) : JOHN MARSHALL MCDONALD It is certified that error appears in the above-identified patent and that said Letters Patent are hereby corrected as shown below:

Column 3, line 12, "the" (second occurrence) should read -- The --.

Column 7, line 1, "19" should read -- 10 --.

line 12, after "SN" insert -- 74148 --.

line 20, after "SN" insert -- 7400 --.

Signed and Sealed this

Twenty-fifth Day of April 1978

[SEAL]

Attest:

RUTH C. MASON
Attesting Officer

LUTRELLE F. PARKER
Acting Commissioner of Patents and Trademarks